United States Patent [19]

Wei

[11] 4,327,221

[45] Apr. 27, 1982

[54] 2-SUBSTITUTED-3-HYDROXY-THIAZOLO(2,3-b)-THIAZOLIUM SALTS AND MESOIONIC DIDEHYDRO DERIVATIVES THEREOF

[75] Inventor: Peter H. L. Wei, Springfield, Pa.

[73] Assignee: American Home Products Corporation, New York, N.Y.

[21] Appl. No.: 197,357

[22] Filed: Oct. 15, 1980

[51] Int. Cl.³ ............................................ C07D 277/60
[52] U.S. Cl. ................................. 548/154; 424/270; 548/152; 548/153
[58] Field of Search ...................... 548/152, 154, 153; 424/270

[56] References Cited

U.S. PATENT DOCUMENTS 4,076,817  2/1978  Acheson et al. .................... 548/154
4,110,460  8/1978  Baetz .................................... 548/154

OTHER PUBLICATIONS

Potts et al., J. Org. Chem. 446221, pp. 3808–3811 (1979).

Primary Examiner—Nicholas S. Rizzo
Attorney, Agent, or Firm—George Tarnowski

[57] ABSTRACT

Novel 2-substituted-3-hydroxythiazolo[2,3-b]thiazolium salts, the mesoionic didehydro derivatives thereof and related compounds and their use as modulators of the immune response are disclosed.

11 Claims, No Drawings

2-SUBSTITUTED-3-HYDROXYTHIAZOLO(2,3-b)-THIAZOLIUM SALTS AND MESOIONIC DIDEHYDRO DERIVATIVES THEREOF

BACKGROUND OF THE INVENTION

The invention relates to novel 2-substituted 3-hydroxythiazolo[2,3-b]thiazolium salts, 2-substituted thiazolo[2,3-b]thiazol-3(2H)-one mesoionic didehydro derivatives, 2-substituted imidazo[2,3-b]thiazolium salts, 2-substituted-pyrrolo[2,1-b]thiazolium salts and related compounds, and their use as modulators of the immune response.

In recent years, the rapid upsurge in immunological research has brought about a greater appreciation and understanding of the complexities of the immune response. While the traditional overall view of the immune system remains, new discoveries have radically changed some thinking about the details of the system. Thus, the immune system is still divided into humoral immunity, populated with B cells and responsible for antibody formation, and cell-mediated immunity, populated with T cells and responsible for the rejection of organ transplants or skin grafts, as well as the defense mechanism against various foreign biological matter and endogenous neoplastic growths.

It is only in the last decade or so, however, that the concept has been accepted that different cell populations interact in the induction and expression of both humoral and cell-mediated immunity. Thus, subpopulations of B cells and T cells have been described, such as for example "suppressor" and "helper" T cells. In a number of animal models, it has been postulated that the helper T cells act in the induction of a complete antibody response to many antigens, whereas T suppressor cells are capable of preventing or terminating such responses. It is now believed that positive and negative cellular interactions control the ultimate degree of immune response. So, it is believed that any given immune response is regulated, and that the degree and mode of regulation may ultimately explain the various reactions, diseases, and disorders which are the manifestations of the operation of the organism's immune system.

The T cell subpopulations of suppressor and helper T cells have been implicated in a number of immune response manifestations. Thus, the loss of suppressor T cells is now believed to be a major factor in such autoimmune connective tissue disease as systemic lupus erythematosus. Moreover, in the latter case, as well as in probably impaired immune system responses such as rheumatoid arthritis, it is believed the helper T cells exacerbate the condition.

Also, the theory has been advanced that T suppressor cell hypofunctioning, resulting in inadequate T-B cell cooperation in the immune response, with continuous B cell stimulation and subsequent antibody production may be the cause of the production of antigen-antibody complexes which are the causative agents of renal and inflammatory processes in arthritis and autoimmune diseases.

Thus, it is now apparent that a number of lymphopoietic disorders are undoubtedly associated with abnormalities of T cell and especially suppressor cell function. The loss of suppressor function is at least an early event in certain immune response diseases and is a disease-perpetuating mechanism in others. The loss of suppressor function probably leads to excessive lymphoid cell proliferation and may significantly contribute to lymphoproliferative disorders. The conditions created thereby may be exacerbated by helper T cells.

The role of immunomodulatory agents in the treatment of immune diseases and disorders, as well as in the attempt to prolong the life of organ transplants and skin grafts, has been to suppress the immune response, especially of cell-mediated immunity. By suppressing the cell-mediated immune response, it is possible to delay and possibly prevent the host organism from rejecting a skin graft or organ transplant, or the graft from immunologically rejecting the host (graft vs. host reaction). Similarly, enhancing or reinstituting suppressor function by immunomodulator therapy is a beneficial course of treatment for antioimmune and probable antoimmune diseases and disorders. However, the current immunosuppressive agents have the serious drawback that in effective doses they suppress the entire immune response. Thus, they suppress both the cell-mediated and humoral immunity, with the result that the patient is left without immunity to infections which he could otherwise readily overcome without medical aid. Thus, the hitherto known immunosuppressive agents are not selective in their action.

The compounds of the present invention, however, are highly selective immunomodulatory agents which are especially indicated in the treatment of various skin graft and organ transplant reactions, and immune system diseases and disorders such as systemic lupus erythematosus and rheumatoid arthritis, whose etiology is probably suppressor T cell dysfunction.

DETAILED DESCRIPTION OF THE INVENTION

The invention is directed to novel compounds having the general formula:

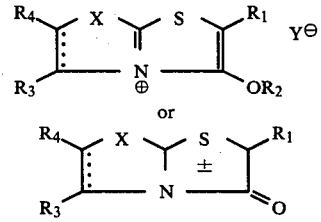

wherein
$R_1$ is phenyl or phenyl substituted with chloro, fluoro, bromo, or lower alkyl;
$R_2$ is hydrogen, lower alkanoyl or the group

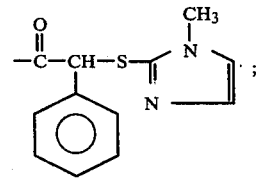

$R_3$ is hydrogen, alkoxycarbonylalkyl of 3 to 10 carbon atoms, phenyl or phenyl substituted with fluoro, chloro, bromo, or lower alkyl;
$R_4$ is hydrogen or alkoxycarbonylalkyl of 3–10 carbon atoms;
X is $CH_2$, S or $NR_5$, wherein $R_5$ is hydrogen or lower alkyl; and
Y is a halide and where the dotted line represents an optional double bond in the 5,6 position.

The term "lower alkyl" when used herein includes straight and branched chain hydrocarbon radicals having from 1 to about 6 carbon atoms. The term "lower alkoxy" in like manner designates radicals in which the hydrocarbon portion has 1 to about 6 carbon atoms.

The term "halide" when used herein refers to radicals of the elements fluorine, chlorine, bromine and iodine.

The compounds of the invention can be readily prepared by a cyclization reaction in which a suitably substituted 2-mercaptothiazole or thiazolidinthione (where X is $CH_2$ a suitably substituted 2-mercaptopyrrole and when X is $NR_5$ a suitably substituted 2-mercaptoimidazole) is condensed with a suitably substituted α-halo acetic acid in the presence of a condensing agent:

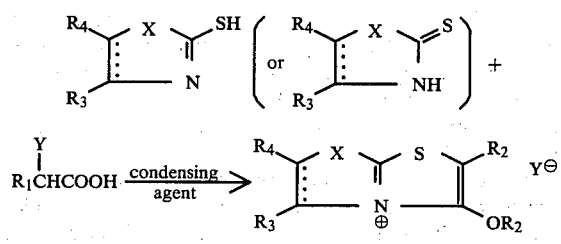

wherein $R_1$, $R_3$, $R_4$, X and Y are as defined hereinbefore, and $R_2$ is either hydrogen or the residue of the condensing agent. The reactants, in an organic solvent, such as for example acetone, and the condensing agents, such as for example a mixture of acetic acid and acetic anhydride, trifluoroacetic anhydride and the like are heated until the solvent volume is reduced and a precipitate is obtained. The precipitated solid is recrystallized to yield the desired thiazolium salt.

In those cases where $R_3$ in the final product thiazolium salt is the condensing agent residue, such as where $R_3$ is acetyl, and where it is desired to obtain the compound in which $R_3=H$, the condensing agent residue can be readily removed by conventional means, as for example deacylation by heating.

The thiazolium salts can be transformed into their mesoionic didehydro derivatives:

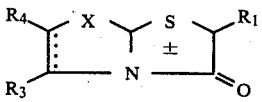

by dissolving the thiazolium salts in a methylene/water mixture, separating the organic and aqueous layers and concentrating the organic (methylene chloride) layer to recover the mesoionic didehydro derivative, which can then be further purified by recrystallization.

The compounds of the invention are immunomodulators having particular activity on the cell-mediated immune system, and they have therapeutic application in a variety of situations in which immunomodulation is indicated. Thus, the compounds are useful in treating allograft reactions, organ transplant reactions and graft vs. host reactions. The compound are also useful in the treatment of autoimmune diseases, such as systemic lupus erythematosus (SLE). Further, the compounds of the invention inhibit the production of the immunoglobulins, which are so pathologic to autoimmune disease, such as SLE, as well as the production of antigen-antibody complexes which are the causative agents of renal and inflammatory processes in arthritis and autoimmune diseases. Thus, the compounds of the invention are also useful in the treatment of such conditions as rheumatoid arthritis.

When the compounds of the invention are employed as immunomodulators, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for injection administration the dose is from about 5 milligrams to about 150 milligrams and for oral administration the dose is from about 25 milligrams to about 250 milligrams and preferably from about 25 milligrams to about 250 milligrams per day either as a single unit dose, or if desired, the dosage may be divided into convenient subunits administered at convenient times throughout the day.

The immunomodulatory effect of the compounds of the invention may be demonstrated by standard pharmacological and histological procedures. The pharmacological procedures are described more fully in the examples given hereinafter.

These procedures illustrate the ability of the compounds of the invention to exert an immunomodulatory effect as evidenced by the hemolytic plaque technique (Jerne Test) and by their ability to prevent the spread of experimental metastatic cancer using survival time techniques.

EXAMPLE 1

3-Acetoxy-5-(4-chlorophenyl)-6-(2-ethoxy-2-oxoethyl)-2-phenylthiazolo[2,3-b]thiazolium bromide A. 4-(4-chlorophenyl)-2-mercapto-5-thiazole acetic acid, ethyl ester 50.0 g. (0.157 m.) 3-bromo-3-p-chlorobenzoylpropionic acid, ethyl ester and 17.5 g. (0.157 m.) ammonium dithiocarbamate in 500 ml. absolute ethanol are heated at gentle reflux for 5 hours. The reaction mixture is allowed to stand at room temperature overnight. The solid which results is dissolved in 800 ml. of methylene chloride and the solution is washed with 500 ml. of water. The methylene chloride layer is dried over anhydrous magnesium sulfate, and after removal of the methylene chloride the residual solid is recrystallized from ethanol. 39.2 g. (80% yield) of title product is obtained, m.p. 176°–178° C.

Analysis for: $C_{13}H_{12}ClNO_2S_2$. Calculated: C, 49.67; H, 3.86; N, 4.46; Cl, 11.30; S, 20.43. Found: C, 49.66; H, 3.69; N, 4.39; Cl, 11.44; S, 20.20.

B. 4-(4-chlorophenyl)-2-mercapto-5-thiazole acetic acid

The product of (A.) above is saponified to give an 88% yield of the title product, m.p. 245°–247° C.

Analysis for: $C_{11}H_8ClNO_2S_2$. Calculated: C, 46.23; H, 2.83; N, 4.90; Cl, 12.41; S, 22.44. Found: C, 45.86; H, 2.67; N, 4.86; Cl, 12.66; S, 22.02.

C. 3-Acetoxy-5-(4-chlorophenyl)-6-(2-ethoxy-2-oxoethyl)-2-phenylthiazolo[2,3-b]thiazolium bromide A mixture of 12.8 g. (0.04 m.) 4-(4-chlorophenyl)-2-mercapto-5-thiazole acetic acid of (B.) above and 8.8 g. (0.04 m.) α-bromophenylacetic acid in 200 ml. acetone and 40 ml. each of glacial acetic acid and acetic anhydride is heated in an open flask for 2 hours. The solvents are removed and the residual solid triturated with acetonitrile. 13.4 g. (61% yield) of title product is obtained, m.p. 175°–180° C.

Analysis for: $C_{23}H_{19}ClNO_4S_2Br$. Calculated: C, 49.96; H, 3.46; N, 2.53; Cl, 6.41. Found: C, 49.65; H, 3.56; N, 2.64; Cl, 6.71.

EXAMPLE 2

3-Acetoxy-2-phenyl-5-carbethoxymethylthiazolo[2,3-b]thiazolium bromide

A mixture of 10.0 g (0.05 m.) 2-mercapto-thiazole-4-acetic acid, ethyl ester (prepared according to U.S. Pat. No. 2,766,238) and 10.75 g. (0.05 m.) α-bromophenylacetic acid in 200 ml. of acetone and 20 ml. each of glacial acetic acid and acetic anhydride is heated in an open flask for two hours. The solvents are removed and the residual solid triturated with acetone. 12 g. of title product is obtained, m.p. 160°–170° C. (dec.).

Analysis for: $C_{17}H_{16}NO_4S_2Br$. Calculated: C, 46.16; H, 3.65; N, 3.17; Br, 18.07. Found: C, 45.86; H, 3.66; N, 3.30; Br, 18.05.

EXAMPLE 3

5-(2-Ethoxy-2-oxoethyl)-3-hydroxy-2-phenyl-thiazolo[2,3-b]thiazolium bromide

The compound of Example 2 is deacetylated to obtain the title compound, m.p. 177°–183° C.

Analysis for: $C_{15}H_{14}NO_3S_2Br$. Calculated: C, 45.00; H, 3.52; N, 3.50. Found: C, 44.94; H, 3.57; N, 3.48.

EXAMPLE 4

3-Acetoxy-5-(4-chlorophenyl)-2-phenylthiazolo[2,3-b]thiazolium bromide

A mixture of 10.0 g. (0.044 m.) 4-(4-chlorophenyl)-2-mercaptothiazole (prepared by the reaction of α-bromo-4-chloroacetophenone with ammonium dithiocarbamate) and 10.0 g. (0.04 m.) α-bromophenylacetic acid in 200 ml. of acetone and 40 ml. each of glacial acetic acid and acetic anhydride is heated for 2 hours. After the solvents are removed, the residual solid is triturated with acetone and the resulting solid collected. 10 g. (58% yield) of the title product is obtained, m.p. 160°–165° C.

Analysis for: $C_{19}H_{13}ClNO_2S_2Br$. Calculated: C, 48.88; H, 2.81; N, 3.00; Cl, 7.60; S, 13.74. Found: C, 48.73; H, 2.89; N, 3.04; Cl, 8.09; S, 13.72.

EXAMPLE 5

5-(4-Chlorophenyl)-3-hydroxy-2-phenylthiazolo[2,3-b]thiazolium bromide

The compound of Example 4 is deacetylated to obtain the title compound, m.p. 150° C. (dec.).

Analysis for: $C_{17}H_{11}ClNOS_2Br$. Calculated: C, 48.07; H, 2.61; N, 3.30. Found: C, 48.01; H, 2.67; N, 3.27.

EXAMPLE 6

5-(2-Ethoxy-2-oxoethyl)-2-phenylthiazolo-[2,3-b]thiazol-3(2$\underline{H}$)-one mesoionic didehydro derivative 7.0 g. (0.0166 m.) 5-(2-ethoxy-2-oxoethyl)-3-hydroxy-2-phenylthiazolo[2,3-b]thiazolium bromide, prepared according to Example 3, is disproportionated in a mixture of methylene chloride and water. The recovered material, after removal of most of the methylene chloride, is recrystallized from acetonitrile. 3.6 g. (68% yield) of the title compound is obtained, m.p. 166°–167° C.

Analysis for: $C_{15}H_{13}NO_3S_2$. Calculated: C, 56.40; H, 4.10; N, 4.38. Found: C, 56.22; H, 4.10; N, 4.38.

EXAMPLE 7

7-Methyl-3-[α-(1-methylimidazol-2-ylthio)-α-phenylacetoxy]-2-phenylimidazo[2,3-b]thiazolium bromide, hydrobromide A 250 ml. glacial acetic acid solution of 6.84 g. (0.06 m.) 2-mercapto-1-methylimidazole and 12.9 g. (0.06 m.) α-bromophenylacetic acid, containing 50 ml. of acetic anhydride, is heated to reflux for ½ hour. The solution is filtered, solvent removed and the residual solid triturated with acetone. The 13.9 g. of collected solid is recrystallized from acetonitrile to give 7.5 g. (40% yield) of title compound, m.p. 175°–176° C.

Analysis for: $C_{24}H_{21}N_4O_2S_2Br \cdot HBr$. Calculated: C, 46.31; H, 3.56; N, 9.00. Found: C, 45.99; H, 3.57; N, 9.17.

EXAMPLE 8

5,6-Dihydro-2-phenylthiazolo[2,3-b]thiazol-3(2$\underline{H}$)-one mesoionic didehydro derivative A glacial acetic acid solution of 11.9 g. (0.10 m.) 2-thiazolidinthione and 21.5 g. (0.10 m.) α-bromophenylacetic acid is heated on a steam bath overnight. After removal of solvent, the residual solid is triturated with ether and the solid is collected. The solid is recrystallized from acetonitrile to give 8.2 g. (35% yield) of title compound, m.p. 150°–151° C.

Analysis for: $C_{11}H_9NOS_2$. Calculated: C, 56.14; H, 3.86; N, 5.95; S, 27.25. Found: C, 56.07; H, 3.85; N, 6.05; S, 26.79.

EXAMPLE 9

2-(4-Chlorophenyl)-5,6-dihydrothiazolo[2,3-b]thiazol-3(2$\underline{H}$)-one mesoionic didehydro derivative 3.57 g. (0.03 m.) 2-thiazolidinthione and 7.50 g. (0.03 m.) α-bromo(p-chlorophenyl)-acetic acid are dissolved in 50 ml. glacial acetic acid and the solution is heated on a steam bath for 5 hours. After filtration the solvent is removed and the residual solid is triturated with ether and the solid is collected. The solid is recrystallized from acetonitrile to give 2.5 g. (31% yield) of title compound, m.p. 188°–189° C.

Analysis for: $C_{11}H_8ClNOS_2$. Calculated: C, 48.97; H, 2.99; N, 5.19; Cl, 13.14; S, 23.77. Found: C, 48.96; H, 2.95; N, 5.21; Cl, 13.25; S, 24.04.

EXAMPLE 10

6,7-Dihydro-3-hydroxy-2-phenyl-5H-pyrrolo[2,1-b]thiazolium bromide

A 50 ml. glacial acetic acid solution of 3.0 g. (0.03 m.) 2-pyrrolidinethione and 6.5 g. (0.03 m.) α-bromophenylacetic acid is heated on a steam bath for 5 hours. The solution is cooled and the precipitated solid is collected and washed with acetone and ether. The 7.0 g. of solid is recrystallized from acetonitrile to give 4.2 g. (47% yield) of title compound, m.p. 200°–205° C.

Analysis for: $C_{12}H_{12}NOS.Br$. Calculated: C, 48.33; H, 4.06; N, 4.70; Br, 26.80; S, 10.75. Found: C, 48.15; H, 4.11; N, 4.85; Br, 27.21; S, 10.79.

EXAMPLE 11

In cell-mediated antoimmune diseases, such as SLE, rheumatoid arthritis (RA), hemolytic anemia and so forth, there is a marked increase in the production of the IgM and IgG immunoglobulins. In the case of SLE and hemolytic anemia, the increase is systemic and appears in the serum, while in the case of rheumatoid arthritis, the increase tends to localize in the synovial fluids. The increase is itself pathologic and so treatment of the disease should be aimed at alleviating the exacerbating effects of the immunoglobulins.

In this example, the compounds of the invention are tested for their effect on antibody-secreting plaque-forming splenocytes (IgG and IgM) in the Cunningham modification of the Jerne assay. This technique is able to detect, in a quantitative manner, antibody producing cells in response to antigen stimulus in the host mouse. For study of cell-mediated immune response, sheep erythrocytes (SRBC) are used (as in the present Example), while for humoral immune response, SRBC coupled with pneumococcal polysaccharide is used.

CDF$_1$ (Balb/c×DBA/2) mice are immunized with 0.1 ml. of $10^8$ sheep erythrocytes (SRBC) intraperitoneally 4–5 days before the assay. The mice are separated into groups, with one group serving as a control and all other groups receiving compounds of the invention. The treated mice are dosed with drug on day one. In order to determine IgM plaques, the mice are sacrificed on day four, and to determine IgG plaques, on day five or six. The spleens of the sacrificed mice are excised and washed several times in RPMI 1640 with 10% fetal bovine serum. 100 λ of spleen cells are mixed with a drop of guinea pig complement, four drops of RPMI 1640 and a drop of 25% SRBC in a microtiter plate well and then pipetted into a Cunningham chamber. On day four, for IgM determinations, the chambers are incubated for 30 minutes at 37° C. Antibody, released by the small proportion of active cells, attaches to the surrounding erythrocytes which are lysed by complement leaving a small plaque up to 0.5 mm. in diameter. Since only cells releasing IgM antibody form plaques directly, a "developing" serum must be added to be able to form and view IgG plaques. Thus fifth or sixth day cultured spleen cells are further treated with rabbit antimouse IgG and then incubated for 45 minutes. Both IgM and IgG plaques are counted under a stereomicroscope. The IgM plaque counts for mice treated with compounds of the invention are presented in Tables 1–3:

TABLE 1

| Compound | Dose, mg/kg | IgM, Mean |
|---|---|---|
| Control (⅓ CMC/saline) | 1.0 ml. | 189,900 ± 7,061 |
| A | 25.0 | 72,900 ± 1,812 |
| B | 25.0 | 103,200 ± 11,651 |
| C | 25.0 | 98,400 ± 13,931 |
| D | 25.0 | 84,300 ± 8,635 |

A = 5-(4-chlorophenyl)-3-hydroxy-2-phenylthiazolo-[2,3-b]thiazolium bromide
B = 5-(2-ethoxy-2-oxoethyl)-2-phenylthiazolo[2,3-b]-thiazol-3(2H)-one mesoionic didehydro derivative
C = 3-acetoxy-5-(4-chlorophenyl)-6-(2-ethoxy-2-oxoethyl)-2-phenylthiazolo[2,3-b]thiazolium bromide
D = 5-(2-ethoxy-2-oxoethyl)-3-hydroxy-2-phenylthiazolo-[2,3-b]thiazolium bromide

TABLE 2

| Compound | Dose, mg/kg | IgM, Mean |
|---|---|---|
| Control (⅓ CMC/saline) | 1.0 ml. | 189,300 ± 11,328 |
| E | 25.0 | 178,410 ± 40,292 |
| F | 25.0 | 128,500 ± 13,143 |
| G | 25.0 | 117,900 ± 4,988 |

E = 5,6-Dihydro-2-phenylthiazolo[2,3-b]thiazol-3-one mesoionic didehydro derivative
F = 6,7-Dihydro-3-hydroxy-2-phenyl-5H-pyrrolo[2,1-b]thiazolium bromide
G = 2-(4-Chlorophenyl)-5,6-dihydrothiazolo[2,3-b]-thiazol-3(2H)-one mesoionic didehydro derivative

TABLE 3

| Compound | Dose, mg/kg | IgM, Mean |
|---|---|---|
| Control (⅓ CMC/saline) | 1.0 ml. | 141,600 |
| C | 100.0 | 100,500 ± 11,224 |
| D | 100.0 | 67,800 ± 3,530 |
| A | 100.0 | 125,500 ± 9,094 |
| B | 100.0 | 148,680 ± 4,608 |

Compound A–D are the same as those listed under TABLE 1.

The results show that the compounds of the invention cause a marked reduction in the production of IgM by antibody secreting lymphocytes in response to antigen, when administered at relatively low dosage levels.

EXAMPLE 12

The compounds of the invention are tested for their ability to inhibit the metastatic spread of the highly virulent Lewis lung tumor.

A 0.1 ml. brei containing $2 \times 10^6$ viable Lewis lung cells is implanted into the right axillary region of 20 gram, male BDF$_1$ (Dba/2×C$_{57}$) mice on day 0. Dosing is on days 1, 3, 7, 9 and 12. All groups receive 5 mg/kg. intraperitoneally. Primary tumors are measured on day 12 and their masses calculated. All survivors are sacrificed by cervical separation. On day 14 the lungs are excised and examined for metastatic involvement using the Wexler technique (Wexler, Hilda: Accurate Identification of Experimental Pulmonary Metastases, *Journal of The National Cancer Institute, Vol.* 36, No. 4, April, 1966).

The results obtained against the primary tumor and the % inhibition of metastatic spread are given in Table 4.

TABLE 4

| Compound | Dose, mg/kg. | No. of Lesions | % Inhibition of Metastases | p-Value |
|---|---|---|---|---|
| Control (⅓ CMC/saline) | — | 20.0 | — | — |
| X | 5.0 | 9.2 | 54 | 0.1 |
| Y | 5.0 | 10.4 | 48 | 0.2 |

TABLE 4-continued

| Compound | Dose, mg/kg. | No. of Lesions | % Inhibition of Metastases | p-Value |
|---|---|---|---|---|
| Z | 5.0 | 12.4 | 38 | 0.3 |

X = 3-Acetoxy-2-phenyl-5-carbethoxymethylthiazolo[2,3-b]-thiazolium bromide

Y = 5-(2-Ethoxy-2-oxoethyl)-3-hydroxy-2-phenylthiazolo[2,3-b]-thiazolium bromide Z = 7-Methyl-3-[α-(1-methylimidazol-2-ylthio)-α-phenyl-acetoxy]-2-phenylimidazo[2,3-b]thiazolium bromide, hydrobromide The results show that some of the compounds of the invention are effective in inhibiting the metastatic spread of Lewis lung tumor.

What is claimed is:

1. A compound having the formula:

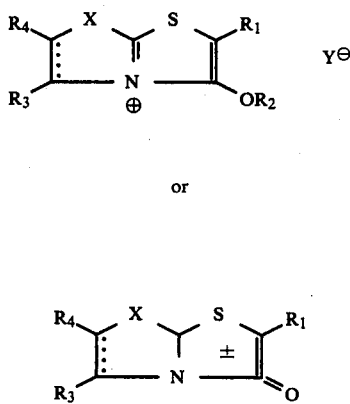

wherein $R_1$ is phenyl or phenyl substituted with chloro, fluoro, bromo or lower alkyl;

$R_2$ is hydrogen, lower alkanoyl or the group

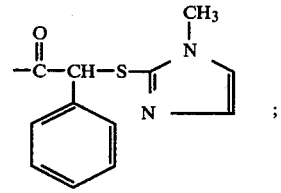

$R_3$ is hydrogen, alkoxycarbonylalkyl of 3 to 10 carbon atoms, phenyl or phenyl substituted with fluoro, chloro, bromo or lower alkyl;

$R_4$ is hydrogen or alkoxycarbonylalkyl of 3-10 carbon atoms;

X is $CH_2$, S or $NR_5$, wherein $R_5$ is hydrogen or lower alkyl; and

Y is a halide and where the dotted line represents an optional double bond in the 5,6-position.

2. The compound of claim 1, having the name 3-acetoxy-5-(4-chlorophenyl)-6-(2-ethoxy-2-oxoethyl)-2-phenylthiazolo[2,3-b]thiazolium bromide.

3. The compound of claim 1, having the name 3-acetoxy-2-phenyl-5-carbethoxymethylthiazolo[2,3-b]thiazolium bromide.

4. The compound of claim 1, having the name 5-(2-ethoxy-2-oxoethyl)-3-hydroxy-2-phenylthiazolo[2,3-b]thiazolium bromide.

5. The compound of claim 1, having the name 3-acetoxy-5-(4-chlorophenyl)-2-phenylthiazolo[2,3-b]thiazolium bromide.

6. The compound of claim 1, having the name 5-(4-chlorophenyl)-3-hydroxy-2-phenylthiazolo[2,3-b]thiazolium bromide.

7. The compound of claim 1, having the name 5-(2-ethoxy-2-oxoethyl)-3-phenylthiazolo[2,3-b]thiazol-3(2H)-one mesoionic didehydro derivative.

8. The compound of claim 1, having the name 7-methyl-3-[α-(1-methylimidazol-2-ylthio)-α-phenylacetoxy]-2-phenylimidazo[2,3-b]thiazolium bromide.

9. The compound of claim 1, having the name 5,6-dihydro-2-phenylthiazolo[2,3-b]thiazol-3(2H)-one mesoionic didehydro derivative.

10. The compound of claim 1, having the name 2-(4-chlorophenyl)-5,6-dihydrothiazolo[2,3-b]thiazol-3(2H)-one mesoionic didehydro derivative.

11. The compound of claim 1, having the name 6,7-dihydro-3-hydroxy-2-phenyl-5H-pyrrolo[2,1-b]thiazolium bromide.

* * * * *